(12) United States Patent
Fechtel et al.

(10) Patent No.: US 6,573,393 B1
(45) Date of Patent: Jun. 3, 2003

(54) METHOD FOR PRODUCING L-ASCORBIC ACID

(75) Inventors: Ulrich Fechtel, Ober-Ramstadt (DE); Wolfgang Heinz, Bensheim (DE); Klaus Beschmann, Reinheim (DE); Bernd Müller, Zwingenberg (DE); Jöran Stoldt, Weiterstadt (DE)

(73) Assignee: Merck KGAA, Darmstadt (DE)

( * ) Notice: Subject to any disclaimer, the term of this patent is extended or adjusted under 35 U.S.C. 154(b) by 0 days.

(21) Appl. No.: 09/890,788

(22) PCT Filed: Jan. 21, 2000

(86) PCT No.: PCT/EP00/00442

§ 371 (c)(1), (2), (4) Date: Aug. 6, 2001

(87) PCT Pub. No.: WO00/46216

PCT Pub. Date: Aug. 10, 2000

(30) Foreign Application Priority Data

Feb. 5, 1999 (DE) .......................................... 199 04 821

(51) Int. Cl.⁷ ............................................. C07D 305/12
(52) U.S. Cl. ...................................................... 549/315
(58) Field of Search ......................................... 549/315

(56) References Cited

FOREIGN PATENT DOCUMENTS

GB          2 205 567 A    * 12/1988

* cited by examiner

Primary Examiner—Amelia Owens
(74) Attorney, Agent, or Firm—Millen, White, Zelano and Branigan, P.C.

(57) ABSTRACT

The invention relates to a method for producing L-ascorbic acid from 2-keto-L-gulonic acid or 2,3-4,6-diacetone-2-keto-L-gulonic acid. The reaction is carried out in the presence of water and hydrogen halide and the concentration of the hydrogen halide in water is greater than 37 wt. %.

21 Claims, No Drawings

METHOD FOR PRODUCING L-ASCORBIC ACID

The invention relates to a process for the preparation of L-ascorbic acid from 2-keto-L-gulonic acid or 2,3-4,6-diacetone-2-keto-L-gulonic acid, the reaction being carried out in the presence of water and hydrogen halide and the concentration of the hydrogen halide in water being greater than 37% by weight.

Preparation processes for L-ascorbic acid based on the reaction of 2-keto-L-gulonic acid or 2,3-4,6-diacetone-2-keto-L-gulonic acid are already known. When employing 2-keto-L-gulonic acid, both the ester process via the stages methyl 2-keto-L-gulonate and sodium ascorbate and direct processes using acids are described in the literature. In the direct process, after enolization and lactonization of 2-keto-L-gulonic acid L-ascorbic acid is obtained. In the direct conversion, in the known processes preferably hydrochloric acid is used as a catalyst. The reaction is usually carried out here in the presence of organic solvents such as toluene, xylene, acetone, chloroform etc. Disadvantages of this known procedure, however, are, for example, the long reaction times and the necessity of the employment and the work-up of solvent mixtures.

The reaction of 2-keto-L-gulonic acid with 36% hydrochloric acid is described, for example, in DE 29 39 052. After reaction at 100° C. and after removal of the hydrochloric acid by distillation, a yield of 87% of theory of L-ascorbic acid is obtained. The disadvantage of the process, however, is the rapid decomposition of the ascorbic acid at 100° C., so that an increased formation of by-products and an intense black coloration of the solution occurs. On account of the large amount of by-products, isolation of the ascorbic acid is associated with further, not inconsiderable losses of material.

The abovementioned problems were partly eliminated according to the process proposed in Patent Specification DE 197 34 086. By lowering the reaction temperature to 40 to 80° C., if the reaction time is simultaneously lengthened and in the presence of 37% hydrochloric acid higher yields of ascorbic acid in solution can be obtained. For example, at a reaction temperature of 58° C. up to 91% of ascorbic acid in solution can be obtained. This solution, however, contains water-insoluble oily by-products and is black-colored, so that before crystallization of the ascorbic acid the by-products and in particular the undesirable black color must be removed either by means of active carbon treatment or else by extraction or washing with an organic solvent. Moreover, for reasons of quality, the crude ascorbic acid obtained after crystallization must again be subjected to a decolorization step, for example a further active carbon treatment, and an additional crystallization.

It was not possible to achieve an improvement in these results by a further lowering of the reaction temperatures when using the process described in DE 197 34 086. A reaction temperature below 50° C. slows, for example, the reaction rate in such a way that the reaction times significantly increase. Moreover, the color-imparting decomposition reactions cannot be suppressed at this reaction temperature. Even at still lower reaction temperatures of 40° C., water-insoluble and intensively black-colored by-products are formed, for example, with an incomplete conversion of the 2-keto-L-gulonic acid (77% yield). The work-up therefore necessitates the prior removal of these by-products.

The object is thus to develop a process for the preparation of L-ascorbic acid from 2-keto-L-gulonic acid or 2,3-4,6-diacetone-2-keto-L-gulonic acid which avoids or at least decreases the disadvantages of the known processes. In particular, a high yield of L-ascorbic acid should be made possible by this process and moreover L-ascorbic acid should be obtained in such a quality that the expenditure on the decolorization of the reaction solution can be kept as low as possible.

Surprisingly, it has now been found that this object is achieved if the process for the preparation of L-ascorbic acid from 2-keto-L-gulonic acid or 2,3-4,6-diacetone-2-keto-L-gulonic acid is carried out such that the reaction takes place in the presence of water and hydrogen halide and the concentration of the hydrogen halide in water is greater than 37% by weight.

The process according to the invention makes possible a very good yield of L-ascorbic acid. The L-ascorbic acid prepared by the process according to the invention is moreover obtained in such a quality that the expenditure on the decolorization of the reaction solution is very low. In addition, the object set can be achieved with short reaction times despite lower reaction temperatures.

2-Keto-L-gulonic acid is preferably used as a starting material for the process according to the invention.

The hydrogen halides HF, HCl, HBr and HI are suitable for the process according to the invention. HCl or HBr is preferably used for the process according to the invention. HCl is particularly preferably used for the process according to the invention.

Saturation concentrations of hydrogen halides in water under atmospheric pressure known from the literature are, for example, 45% by weight for HCl at 0° C., 42.7% by weight at 25° C., 40.2% by weight at 30° C., 38.9% by weight at 40° C., 37.3% by weight at 50° C. and 35.9% by weight at 60° C., 68.9% by weight for HBr at 0° C., and 66% by weight at 25° C. and 90% by weight for HI at 0° C., and 70% by weight at 10° C. The saturation concentration of the hydrogen halides in water can be determined according to known methods.

The process according to the invention can be carried out, for example, by introducing 2-keto-L-gulonic acid or 2,3-4,6-diacetone-2-keto-L-gulonic acid and hydrogen halide into an autoclave, the hydrogen halide customarily being used in commercially available form (HCl, for example, in the form of a 37% by weight aqueous solution, which in the context of the present invention is also referred to as conc. hydrochloric acid). Gaseous undiluted hydrogen halide is then added or passed in until the desired concentration of the hydrogen halide in water has been achieved.

Alternatively, for example, 2-keto-L-gulonic acid or 2,3-4,6-diacetone-2-keto-L-gulonic acid and water may also be introduced into an autoclave and, after closing the autoclave, such an amount of undiluted hydrogen halide in liquid form can be added or passed in so that the desired concentration of the hydrogen halide in water is achieved.

Undiluted hydrogen halide in the context of the present invention in particular means that the hydrogen halide contains no or only a little water.

For carrying out the reaction, the reaction mixture, after the addition or the introduction of the gaseous or liquid undiluted hydrogen halide, is brought to reaction temperature, if appropriate by warming, and left at this temperature for a certain period of time.

For the process according to the invention, reaction temperatures of 0 to 60° C. are suitable. The reaction is preferably carried out at temperatures of 25 to 50° C. and particularly preferably at temperatures of 35 to 45° C.

When using the hydrogen halides HF, HBr and HI, the process according to the invention is preferably carried out under atmospheric, pressure. When using the hydrogen halide HCl, the process according to the invention, however, is carried out at a pressure which is increased in comparison to atmospheric pressure. This pressure is particularly preferably from 10 to 100 bar and especially preferably from 10 to 50 bar. When carrying out the process according to the invention, the pressure can be up to 150 bar.

The reaction can be carried out either batchwise or continuously. A continuous procedure is preferred, however, with complete dissolution of the 2-keto-L-gulonic acid, as by this means time regimes can be better kept to. The continuous procedure preferably takes place in a pressure-tight flow tube. The process can additionally be significantly simplified if the hydrogen halide needed for the reaction is recycled again by distillation and compression. In this preferred embodiment of the process, the need for hydrogen halide is low.

The process according to the invention as exemplified by 2-keto-L-gulonic acid and the particularly preferred hydrogen halide HCl is described in greater detail below. For 2,3-4,6-diacetone-2-keto-L-gulonic acid and the other hydrogen halides, the process according to the invention, however, can be carried out analogously.

The proportion of the 2-keto-L-gulonic acid in the mixture employed before the introduction of the hydrogen chloride can be from 15 to 97% by weight based on the total mixture employed before the introduction of the hydrogen chloride. The proportion of the 2-keto-L-gulonic acid before the introduction of the hydrogen chloride is preferably from 30 to 40% by weight based on the total mixture employed before the introduction of the hydrogen chloride.

Hydrogen chloride is preferably introduced at temperatures from 0 to 60° C., particularly preferably at temperatures from 0 to 30° C. and especially preferably at approximately 15 to 25° C., the reaction mixture is brought to the desired reaction temperature, if appropriate by warming, and left at this temperature for a certain period of time.

The process can be designed such that the 2-keto-L-gulonic acid is present as a solid or as a solution in water or aqueous HCl before the introduction of the hydrogen chloride. Depending on the amount of water introduced or of aqueous HCl introduced, HCl concentrations up to almost 100% by weight HCl in water can be achieved.

However, even when employing 2-keto-L-gulonic acid as a solid, a low content of water is useful, preferably at least 3% by weight of water based on the 2-keto-L-gulonic acid employed, as traces of water are essential for the reaction. The lower the contents of water in the reaction mixture, the longer the reaction proceeds. Obviously, the 2-keto-L-gulonic acid reacts only in the dissolved state. Taking into account this finding, the amounts of water can otherwise be varied over wide concentration ranges.

After addition of all reaction components, the concentration of hydrogen chloride in water is preferably from 40 to 90% by weight, particularly preferably from 42.7 to 90% by weight and especially preferably from 45 to 65% by weight.

The hydrogen halides HF, HBr and HI can be used for the process according to the invention, for example, in commercially available concentrations in water, e.g. HBr and HI in concentrations of approximately 47 to 48% by weight in water and HF in concentrations of approximately 45 to 70% by weight in water. If higher concentrations than the above-mentioned concentrations are desired for carrying out the process according to the invention using HF, HBr and HI, the desired concentration of the hydrogen halide in water can be adjusted by addition of gaseous or liquid undiluted hydrogen halide. In the case of the hydrogen halide HCl, the desired concentration of HCl in water is preferably adjusted by addition of gaseous or liquid undiluted hydrogen halide.

After addition of all reaction components, the weight ratio of hydrogen chloride to 2-keto-L-gulonic acid is preferably from 0.5:1 to 8:1 and particularly preferably from 2:1 to 4:1.

After addition of all reaction components, the weight ratio of water to 2-keto-L-gulonic acid is preferably from 3:100 to 100:10 and particularly preferably from 1:2 to 3:1.

The process according to the invention can also be carried out under supercritical conditions. For example, for HCl gas supercritical conditions are achieved at 51° C. and 80 bar.

Customarily, the reaction can be discontinued when using all hydrogen halides after approximately 1 to 4 hours by pressure release and possible cooling of the reaction mixture. The continuation or the end of the reaction can also be checked by suitable sampling and analysis of the sample by means of HPLC or iodometry.

The work-up of the batches can be carried out for all hydrogen halides after pressure release by removal of the hydrogen halide, for example by distillation. The resulting solid can optionally be suspended using an organic solvent, for example an alcohol, preferably butanol, so that both the color-imparting substances present in small quantities and residues of the hydrogen halide can be removed with a subsequent distillation.

Examples are listed below which are intended to illustrate the invention without restricting it.

After the isolation of the L-ascorbic acid, the yield was determined by means of iodometry of the L-ascorbic acid either in solution or as a solid.

EXAMPLES

Process Variant A

Example 1

3 g of 2-keto-L-gulonic acid are introduced into a glass insert and 9 g of conc. hydrochloric acid are then added thereto. After closing the autoclave, hydrogen chloride is introduced until a pressure decrease no longer occurs due to the dissolution of the HCl in the aqueous phase (about 20 min). The autoclave is then warmed to 30° C. in the course of 0.5 h and kept at this temperature for three hours (pressure about 43 bar). After cooling and depressurizing the autoclave, the reaction mixture is concentrated on a rotary evaporator. Toward the end, an almost white crystalline material is obtained, which is taken up in butanol again to remove traces of acid and then in turn brought to a residue (yield: 82% of theory).

Example 2

3 g of 2-keto-L-gulonic acid are introduced into a glass insert and 9 g of conc. hydrochloric acid are then added thereto. After closing the autoclave, hydrogen chloride is introduced until a pressure decrease no longer occurs due to the dissolution of the HCl in the aqueous phase (about 20 min). The autoclave is then warmed to 40° C. in the course of 0.5 h and kept at this temperature for three hours (pressure about 45 bar). After cooling and depressurizing the autoclave, the reaction mixture is concentrated on a rotary evaporator. Toward the end, a pale gray crystalline material is obtained, which is taken up in butanol again to remove traces of acid and then in turn brought to a residue (yield: 87.1% of theory).

Example 3

2 g of 2-keto-L-gulonic acid are introduced into a glass insert and 9 g of conc. hydrochloric acid are then added thereto. After closing the autoclave, hydrogen chloride is introduced until a pressure decrease no longer occurs due to the dissolution of the HCl in the aqueous phase (about 20 min). The autoclave is then warmed to 42° C. in the course of 0.5 h and kept at this temperature for three hours (pressure about 45 bar). After cooling and depressurizing the autoclave, the reaction mixture is concentrated on a rotary evaporator. Toward the end, a pale gray crystalline material is obtained, which is taken up in butanol again to remove traces of acid and then in turn brought to a residue (yield: 95% of theory).

Example 4

3 g of 2-keto-L-gulonic acid are introduced into a glass insert and 9 g of conc. hydrochloric acid are then added thereto. After closing the autoclave, hydrogen chloride is introduced until a pressure decrease no longer occurs due to the dissolution of the HCl in the aqueous phase (about 20 min). The autoclave is then warmed to 42° C. in the course of 0.5 h and kept at this temperature for three hours (pressure about 45 bar). After cooling and depressurizing the autoclave, the reaction mixture is concentrated on a rotary evaporator. Toward the end, a pale gray crystalline material is obtained, which is taken up in butanol again to remove traces of acid and then in turn brought to a residue (yield: 93.3% of theory).

Example 5

40 g of 2-keto-L-gulonic acid are introduced into a glass insert and 180 g of conc. hydrochloric acid are then added thereto. After closing the autoclave, hydrogen chloride is introduced until a pressure decrease no longer occurs due to the dissolution of the HCl in the aqueous phase (about 20 min). The autoclave is then warmed to 42° C. in the course of 0.5 h and kept at this temperature for three hours. After cooling and depressurizing the autoclave, the reaction mixture is concentrated on a rotary evaporator. Toward the end, a pale gray crystalline material is obtained, which is taken up in butanol again to remove traces of acid and then in turn brought to a residue (yield: 93.3% of theory).

Example 6

50 g of 2-keto-L-gulonic acid are introduced into a glass insert and 150 g of conc. hydrochloric, acid are then added thereto. After closing the autoclave, hydrogen chloride is introduced until a pressure decrease no longer occurs due to the dissolution of the HCl in the aqueous phase (about 20 min; about 60 g of HCl). The autoclave is then warmed to 42° C. in the course of 0.5 h and kept at this temperature for three hours. After cooling and depressurizing the autoclave, the reaction mixture is concentrated on a rotary evaporator. Toward the end, a pale gray crystalline material is obtained, which is taken up in butanol again to remove traces of acid and then in turn brought to a residue (yield: 92.3% of theory).

Example 7

3 g of 2-keto-L-gulonic acid are introduced into a glass insert and 9 g of conc. hydrochloric acid are then added thereto. After closing the autoclave, hydrogen chloride is introduced until a pressure decrease no longer occurs due to the dissolution of the HCl in the aqueous phase (about 20 min). The autoclave is then warmed to 45° C. in the course of 0.5 h and kept at this temperature for two hours (pressure about 45 bar). After cooling and depressurizing the autoclave, the reaction mixture is concentrated on a rotary evaporator. Toward the end, a pale brown crystalline material is obtained, which is taken up in butanol again to remove traces of acid and then in turn brought to a residue (yield: 87.7% of theory).

Process Variant B

Example 8

50 g of 2-keto-L-gulonic acid are introduced into a glass insert and 12 g of water are then added thereto. After closing the autoclave, 208 g of hydrogen chloride are introduced in liquid form. The autoclave is then warmed to 50° C. in the course of 0.5 h and kept at this temperature for two hours. After the warming-up phase, a pressure of about 80 bar is set. After the cooling and depressurization of the autoclave, the reaction mixture is concentrated on a rotary evaporator. Toward the end, a gray-brown crystalline material is obtained, which is taken up in butanol again to remove traces of acid and then in turn brought to a residue (yield 75.3% of theory).

Example 9

50 g of 2-keto-L-gulonic acid are introduced into a glass insert and 12 g of water are then added thereto. After closing the autoclave, 110 g of hydrogen chloride are introduced in liquid form. The autoclave is then warmed to 45° C. in the course of 0.5 h and kept at this temperature for three hours. After the warming-up phase, a pressure of about 76 bar is set. After the cooling and depressurization of the autoclave, the reaction mixture is concentrated on a rotary evaporator. Toward the end, a gray-brown crystalline material is obtained, which is taken up in butanol again to remove traces of acid and then in turn brought to a residue (yield 83.3% of theory).

Comparative Examples

Example A

Comparative Example with 37% Hydrochloric Acid at 40° C. and Normal Pressure 100 g of 2-ketogulonic acid are introduced into 300 g of 37% hydrochloric acid. The batch is then heated to 40° C. and kept at this temperature for about 4 h. A black-brown-colored solution is obtained. The iodometric determination of the L-ascorbic acid content shows a yield of 77.4% of theory.

Example B

Comparative Example with 37% Hydrochloric Acid at 60° C. and Normal Pressure:

100 of 2-ketogulonic acid are introduced into 300 g of 37% hydrochloric acid. The batch is then heated to 59–60° C. and kept at this temperature for about 3 h. A black-colored solution is obtained. The iodometric determination of the L-ascorbic acid content shows a yield of 90.2% of theory.

What is claimed is:

1. A process for the preparation of L-ascorbic acid from 2-keto-L-gulonic acid or 2,3-4,6-diacetone-2-keto-L-gulonic acid, characterized in that the reaction is carried out in the presence of water and hydrogen halide and the concentration of the hydrogen halide in water is greater than 37% by weight.

2. The process as claimed in claim 1, characterized in that the reaction temperature is from 0 to 60° C.

3. (Amended) The process as claimed in claim 1, characterized in that it is carried out in a continuous procedure.

4. The process as claimed in claim 1, characterized in that the hydrogen halide is recycled.

5. The process as claimed in claim 1, characterized in that the desired concentration of the hydrogen halide in water is set by addition of gaseous or liquid undiluted hydrogen halide.

6. The process as claimed in claim 1, characterized in that the hydrogen halide used is HCl.

7. The process as claimed in claim 6, characterized in that the pressure is increased in comparison to atmospheric pressure.

8. The process as claimed in claim 1, wherein the concentration of the hydrogen halide in water of a reaction mixture is greater than 37% by weight.

9. The process as claimed in claim 1, wherein the hydrogen halide is HF, HBr or HI.

10. The process as claimed in claim 1, wherein the hydrogen halide is HBr.

11. The process as claimed in claim 1, wherein a reaction temperature is 25–50° C.

12. The process as claimed in claim 1, wherein a reaction temperature is 35–45° C.

13. A process for the preparation of L-ascorbic acid from 2-keto-L-gulonic acid or 2,3-4,6-diacetone-2-keto-L-gulonic acid, comprising carrying out a reaction in a reaction mixture comprising water and a hydrogen halide wherein the concentration of the hydrogen halide in the water of the reaction mixture is greater than 37% by weight.

14. The process as claimed in claim 1, wherein a reaction pressure is up to 150 bar.

15. The process as claimed in claim 1, wherein a reaction pressure is about atmospheric pressure.

16. The process as claimed in claim 6, wherein a hydrogen chloride in water of a reaction mixture is 40–90% by weight.

17. The process as claimed in claim 6, wherein a hydrogen chloride in water of a reaction mixture is 42.7–90% by weight.

18. The process as claimed in claim 6, wherein a hydrogen chloride in water of a reaction mixture is 45–65% by weight.

19. The process as claimed in claim 6, wherein the weight ratio of hydrogen chloride to 2-keto-L-gulonic acid is 0.5:1–8:1.

20. The process as claimed in claim 6, wherein the weight ratio of hydrogen chloride to 2-keto-L-gulonic acid is 2:1–4:1.

21. A process for the preparation of L-ascorbic acid from 2-keto-L-gulonic acid or 2,3-4,6-diacetone-2-keto-L-gulonic acid, comprising carrying out a reaction consisting essentially of water and a hydrogen halide wherein the concentration of the hydrogen halide in water of a reaction mixture is greater than 37% by weight.

* * * * *